United States Patent
Connelly et al.

(10) Patent No.: US 6,995,013 B2
(45) Date of Patent: Feb. 7, 2006

(54) CELL-SCAFFOLD COMPOSITION CONTAINING FIVE LAYERS

(75) Inventors: Patrick R. Connelly, Rochester, NY (US); Omotunde M. Babalola, Long Island, NY (US)

(73) Assignee: BioMed Solutions, LLC, West Henrietta, NY (US)

( * ) Notice: Subject to any disclaimer, the term of this patent is extended or adjusted under 35 U.S.C. 154(b) by 669 days.

(21) Appl. No.: 10/190,874

(22) Filed: Jul. 8, 2002

(65) Prior Publication Data

US 2004/0005297 A1 Jan. 8, 2004

(51) Int. Cl.
- *C12N 5/06* (2006.01)
- *C12N 5/08* (2006.01)
- *C12N 11/02* (2006.01)
- *C12N 11/08* (2006.01)
- *A61F 2/00* (2006.01)

(52) U.S. Cl. ............... 435/395; 424/93.7; 424/423; 435/177; 435/180; 435/289.1

(58) Field of Classification Search ............ 424/93.7, 424/423; 435/177, 180, 289.1, 395
See application file for complete search history.

(56) References Cited

U.S. PATENT DOCUMENTS

| | | |
|---|---|---|
| 5,770,417 A | 6/1998 | Vacanti et al. |
| 2004/0158289 A1 | 8/2004 | Girouard |
| 2004/0158290 A1 | 8/2004 | Girouard |

OTHER PUBLICATIONS

Journal of Othopedic Research, ",", Journal of Orthopedic Research, No. 2, p. 286–293, ( Mar. 30, 2001).

Yost, MJ et al., "Design and Construction of a Uniaxial Cell Stretcher," Am J Physiol Heart Circ Physiol, No. 279, p. H3124–3130, ( Sep. 30, 2000).

Bioelectromagnetics, ",", Bioelectromagnetics, No. 20, p. 177–182, ( Sep. 30, 1999).

*Primary Examiner*—David M. Naff
(74) *Attorney, Agent, or Firm*—Howard J. Greenwald

(57) ABSTRACT

A cell-scaffold composition that comprised of at least five layers of biocompatible material, each of which layers is coated with a biological sealant material and contains different cells The cell-scaffold composition is located in a bioreactor that contains devices for mechanically stimulating each of the cells in each of the layers at distinct frequencies.

20 Claims, 12 Drawing Sheets

CELL-SCAFFOLD COMPOSITION CONTAINING FIVE LAYERS

FIELD OF THE INVENTION

A cell-scaffold composition prepared in vitro for regulation of cell differentiation and proliferation, producing functional vascularized organ tissue in vivo. The cell-scaffold composition is disposed within a bioreactor that contains a device for mechanically stimulating the cells in vitro.

BACKGROUND OF THE INVENTION

U.S. Pat. No. 5,770,417 of Joseph P. Vacanti et al. discloses and claims a cell-scaffold composition that is prepared in vitro for implanting in order to produce functional organ tissue in vivo. The scaffold of this patent is three-dimensional and is composed of porous and/or solid fibers of biocompatible, synthetic polymer that are preferably biodegradable. The entire disclosure of this United States patent is hereby incorporated by reference into this specification.

The scaffold of the Vacanti et al. patent does not provide an environment that encourages cells to differentiate and form specific structures. It is an object of this invention to provide such a scaffold.

The replacement of living tissue with living tissue that is specifically designed and constructed to meet the needs of each individual patient is a new alternative for the replacement of totally artificial substitutes points), non-living processed tissue (heart valves) or tissue taken from another site from the patients themselves or other patients (autografts and allografts). Tissue engineering is an interdisciplinary field that applies the principles of engineering and the life sciences toward the development of biological substitutes that restore, maintain, or improve tissue function. Tissue engineered devices can also use controlled drug-delivery methods to release growth factors that may augment angiogenesis or aid in new tissue generation. Most of the materials used as substrates or encapsulated materials for mammalian cells are either synthetic material (such as lactic glycolic acid or polyacrylinotrile-polyvinyl chloride) or other natural substances (such as hydroxyapatite, or alginate). Natural materials are preferred for the in vivo extracellular matrix components for cells because they possess natural interactive properties, such as cell adhesiveness.

In tissue engineering, synthetic biodegradable polymers are used as templates for cells to form permanent new tissues. Systems are designed with highly porous structures to meet the needs for the mass transfer of large number of cells. Angiogenesis after implantation produces permanent vascularized new tissue.

In the intramembranous process of bone formation, bone develops within a vascularized layer of connective tissue. In this process, mesenchymal cells differentiate into osteoblasts, osteoblasts secrete osteoid, and osteoid then mineralizes to form bone spicules. Growth occurs through preferential deposition and resorption of bone. During the endochondral process of bone formation, a hyaline cartilage framework is formed first, and it then is removed and replaced by bone. In this process, chondrocytes (i.e. cartilage forming cells) hypertrophy and secrete extracellular matrix. This matrix becomes calcified. Osteoblasts deposit osteoid on the calcified cartilage cores, and the osteoid is then mineralized to form bone. Types of bone include cortical bone and trabecular bone. Cortical bone, having an approximate density of 1.8 grams per cubic centimeter, is located predominantly as a shell on bone structures; and trabecular bone, having a density of 0.1–1.0 grams per cubic centimeter, can be seen within flat bone (e.g. facial bone), vertebral bodies amongst other places.

In cortical bone, there exist vascular channels in the forms of horizontal Volkman canals, vertical Haversian canals and lacunae for the delivery of nutrients via blood. Thus, provided within the scaffold will be a network of biodegradable, nanoporous interconnected tubules that function as the delivery mechanism until blood vessels have grown in situ. The Haversian canal in the center of the osteon has a diameter ranging between from about 50 to 90 microns. Within the Haversian canal is a blood vessel, typically 15 microns in diameter. Since nutrients which are necessary to keep cells and tissues alive can diffuse a limited distance through mineralized tissue, these blood vessels are necessary for bringing nutrients within a reasonable distance (about 150 microns) of osteocytes or bone cells which exist interior to the bone tissue. In addition to blood vessels, Haversian canals contain nerve fibers and other bone cells called bone-lining cells. Bone lining cells are osteoblasts that have taken on a different shape following the period in which they have formed bone.

The second level cortical bone structure consists of those entities, which make up the osteons in primary and secondary bone, and the "bricks" in plexiform bone. Woven bone is again distinguished by the fact that no discernible entities exist at the second structural level. Within osteonal (primary and secondary) and plexiform bone, the four major matrix second level structural entities are lamellae, osteocyte lacunae, osteocyte canaliculi, and cement lines. Lamellae are bands or layers of bone generally between 3 and 7 microns in thickness. The lamellae are arranged concentrically around the central Haversian canal in osteonal bone. In plexiform bone the lamellae are sandwiched in between non-lamellar bone layers. These lamellae contains Type I collagen fibers and mineral.

The osteocyte lacunae and canaliculi are holes within the bone matrix that contain bone cells called osteocytes and their processes. Osteocytes evolve from osteoblasts, which become entrapped in bone matrix during the mineralization process. As such, the size of osteocyte lacunae is related to the original size of the osteoblast from which the osteocyte evolved. Osteocyte lacunae have ellipsoidal shapes. The maximum diameter of the lacunae generally ranges between about 10 to 20 microns. Within the lacunae, the osteocytes sit within extracellular fluid. Canaliculi are small tunnels, which connect one lacunae to another lacunae. Canalicular processes, starting at osteocytes, travel through other osteocytes canaliculi to connect osteocytes. Those skilled in the art believe that these interconnections provide a pathway through which osteocytes can communicate information about deformation states and thus in some way coordinate bone adaptation.

It is an object of this invention to provide a novel scaffold for the growth of tissues/organs both in vitro and in vivo. In particular, it is an object of this invention to provide a biodegradable scaffold of multiple layers made preferably with collagen or collagen composite material to be placed in either a bioreactor or a directly into a living bio-organism for the purpose of replacing a damaged and/or missing organ such as bone, wherein the scaffold is comprised of mechanical means for stimulating cells.

SUMMARY OF THE INVENTION

In accordance with this invention, there is provided a cell-scaffold composition wherein said cell-scaffold composition is comprised of at least five layers of material, wherein each of said layers is coated with an adhesive material, wherein each of said layers is comprised of different cells, and wherein said cell-scaffold composition is disposed within a bioreactor which is comprised of means are for stimulating each of the cells in each of said layers at distinct frequencies.

BRIEF DESCRIPTION OF THE DRAWINGS

The invention will be described by reference to the following drawings, in which like numerals refer to like elements, and in which.

DESCRIPTION OF THE PREFERRED EMBODIMENTS

Figure 1:
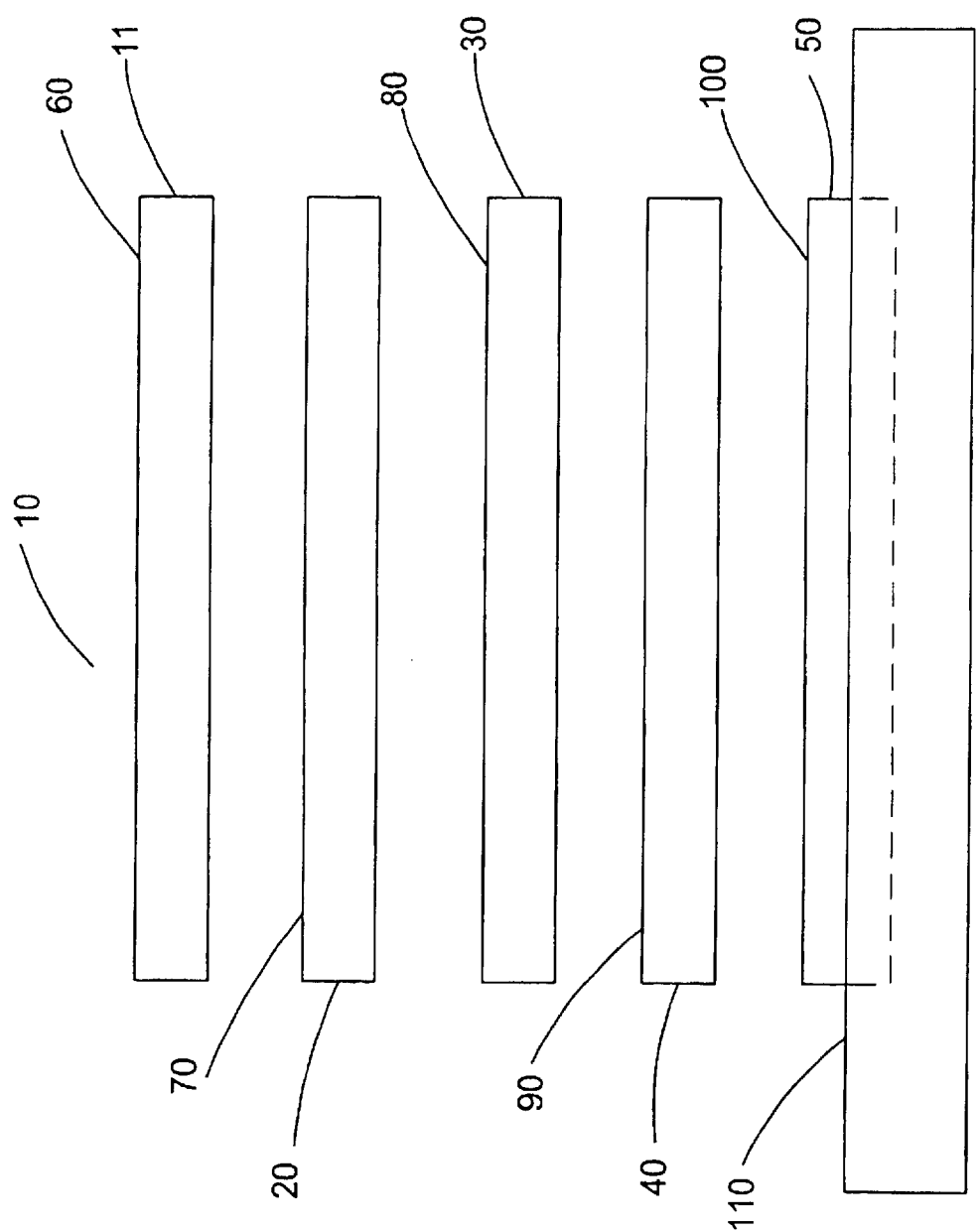
FIG. 1 is an exploded view of one preferred scaffold of the invention.

A cell-scaffold composition prepared in vitro for growing cells to produce functional vascularized organ tissue in vivo is provided in one embodiment of this invention. Each layer is preferably imbedded with cells specific to the organ, growth factors, hormones, gene therapies and other substances that will regulate gene transcription, protein translation, and cellular proliferation and differentiation. Also included within the scaffold of this invention, in another embodiment, is a means for the delivery of nutrients, growth hormones and factors and other like substances in the form of a vascular system acting as an extension of the microcirculation within the growing tissues.

In one embodiment, the cell-scaffold composition is comprised of a multiplicity of layers including a first base layer comprised of an extracellular matrix composition, said first base layer having a porosity of from about 50% to about 90%; and a second layer disposed above and preferably contiguous with said base layer is comprised of angiogenic cells (specifically endothelial and/or smooth muscle cells), said second layer having a porosity of from about 10% to about 50%.

In one embodiment, the second layer has incorporated directly into its matrix angiogenic compounds which are slowly released as the matrix degrades in vivo so that, as the cell-polymer structure is vacularized and the scaffold degrades, the cells differentiate into their inherent characteristics (the cells which would normally form tubules within the body will shape themselves into structures resembling tubules and nerve cells will extend along an appropriately constructed pathway).

In the cell scaffold of this invention, and in one embodiment thereof, a third layer is disposed above and is preferably contiguous with said second layer. This third layer comprises biological material and has a porosity of from about 5% to about 10%, with an average pore diameter ranging from 100–600 microns and their interconnections averaging about 260 microns in diameter. The biomaterial preferably comprises scaffold material, which include the likes of coralline hydroxyapatite, calcium carbonate, poly (lactic acid) (PLA), poly(glycolic acid) (PGA), as well as copolymers of PLA and PGA and in some cases poly (propylene fumarate) and polyarylates, growth factors, interleukins and cytokines such as IGF-I, FGF, PDGF and IL-3 (amongst a vast many others) which have been sintered onto the scaffold or a solution of which the scaffold has been incubated in. The biomaterial can be any combination of the above and related materials that aid in cell growth, proliferation and differentiation.

The cells (mentioned in the previous paragraphs) which are to be implanted on the scaffold layers can be of any cell type with its corresponding growth factors, proliferation and differentiation substances. The science of tissue engineering applies to all cells types and organs in need of replacement. In addition, the biodegradable scaffold may differ for different cells types; thus those listed in this patent are provided only as examples. For the purposes of illustration only, bone will be used in this patent as an example of an application of said methods and device(s).

Bone replacement materials are based on calcium phosphate ceramics because these are related chemically to the mineral phase of natural bone and are bioactive. Natural bone chiefly consists of hydroxyapatite, a calcium phosphate having the empirical formula $Ca_5(PO_4)_3OH$, an organic matrix (which includes Type I collagen fibers), and water.

Collagen provides a well-organized and insoluble scaffold for the deposition of mineral. The breakdown of collagen involves the production of by-products that, among other things, provide the possibility of assessing the rate of the synthesis of the collagen.

The scaffold is preferably produced via a salt leaching technique. The aforementioned layers are representative of the different layers in organs where for example in bone, the layers include periosteal layer, the outer circumferential lamellae, the middle layer (comprising of the interstial lamellae, Harvesian systems—osteons, the Harvesian and Volkman canals and a network of blood vessels), the inner circumferential lamellae and the endosteal layer.

In the regeneration of bone, the aforementioned five layers will preferably be in concentric circles to better mimic actual living bone. It should be noted that the network of blood vessels transverses the entirety of the layers in order to provide sufficient nutrients to maintain the viability of the cells.

Distributed within the layers of the scaffold, there is preferably provided collagen, fibril forming collagen, interleukin 1 (IL-1), ascorbic acid, Matrix Gla proteins, osteocalcin, and such other substances. For growth and proliferation, the cells of the bone are preferably suspended in concentrations of growth factors, including (a) insulin-like growth factors (which promote the formation of osteoblast in bone marrow, synthesis of bone matrix in organ cultures and up-regulate type 1 collagen expression Type 1 collagen), (b) transforming growth factors-beta (TGF$_\beta$superfamily) including Bone Morphogenetic proteins (BMPs) which affect cell growth and proliferation, apoptosis and differentiation and induction of new gene expression, (c) bio-morphogenetic proteins which initiate the migration of mesenchymal cells and their differentiation to chondrobalsts and chondrocytes and mineralization of cartilage, angiogenesis, osteoblast differentiation, bone formation and subsequently, remodeling of the bone, (d) fibroblast growth factors (FGF), (e) platelet derived growth factors (PDGF), (f) vascular endothelial growth factors, (g) epidermal growth factors, and the like. The growth factors can be present in the bone replacement material according to the invention in a concentration of 1 nanogram per cubic centimeter to about 1 milligram per cubic centimeter. The choice of concentration within the range mentioned will often depend on the nature and form of the activity of the growth factor to be employed in each individual case, and on the nature of the scaffold material and its possibly inherent bioactivity.

In one embodiment, the concentration of fibroblast growth factor is preferably within the range of 1 microgram per cubic centimeter to 100 micrograms per cubic centimeter. For the regulation of physiologic and skeletal metabolism, prostaglandins and leukotrienes are preferably added to the scaffold.

In one embodiment, the invention relates to a cell-scaffold composition that is prepared in vitro for implanting in order to produce functional organ tissue in vivo and provides methods for monitoring the progress of the implant in vivo.

In one embodiment, the implant functions as would the biological organ it is meant to replace.

The implant of this invention may be used as a replacement of endogenously occurring parts of systems in a living organisms which have reduced, ceased in function or cease to exist, thereby causing limited functionality of the organism.

FIG. 1 is an exploded view of one preferred scaffold 10 of the invention, which, in the embodiment depicted, is a sagittal view of the scaffold 10 on which specific cells (not shown), corresponding to the organ desired, are to be seeded onto. As is known to those skilled in the art, and referring to the embodiment depicted, the structure 10 is properly referred to as a scaffold. Scaffolds are manufactured by mechanically assembling individual prefabricated layers (or, in general, volumetric elements) of scaffolding with fasteners. The prefabricated sections can first be manufactured using techniques including solvent casting, fiber bonding, melt molding, three-dimensional printing, SFF(Solid Freeform Fabrication), machining hydroxyapatite (HA), and molding collagen. In a preferred embodiment, following preparation of the individual sections of the scaffold, each prefabricated section is seeded with cells before final assembly. In this way, cell viability is not compromised, as destructive heat or chemicals are not involved in the scaffold assembly process. Furthermore, prefabricated vessel constructs can be embedded and assembled into the scaffold as it is being built up to aid in the vascularization of the growing organ. Reference may be had. e.g., to U.S. Pat. Nos. 6,143,293, 6,228,117, 6,176,874, 5,770,417, 6103255, and the like. The disclosure of each of these patents is hereby incorporated by reference into this specification.

Figure 2:
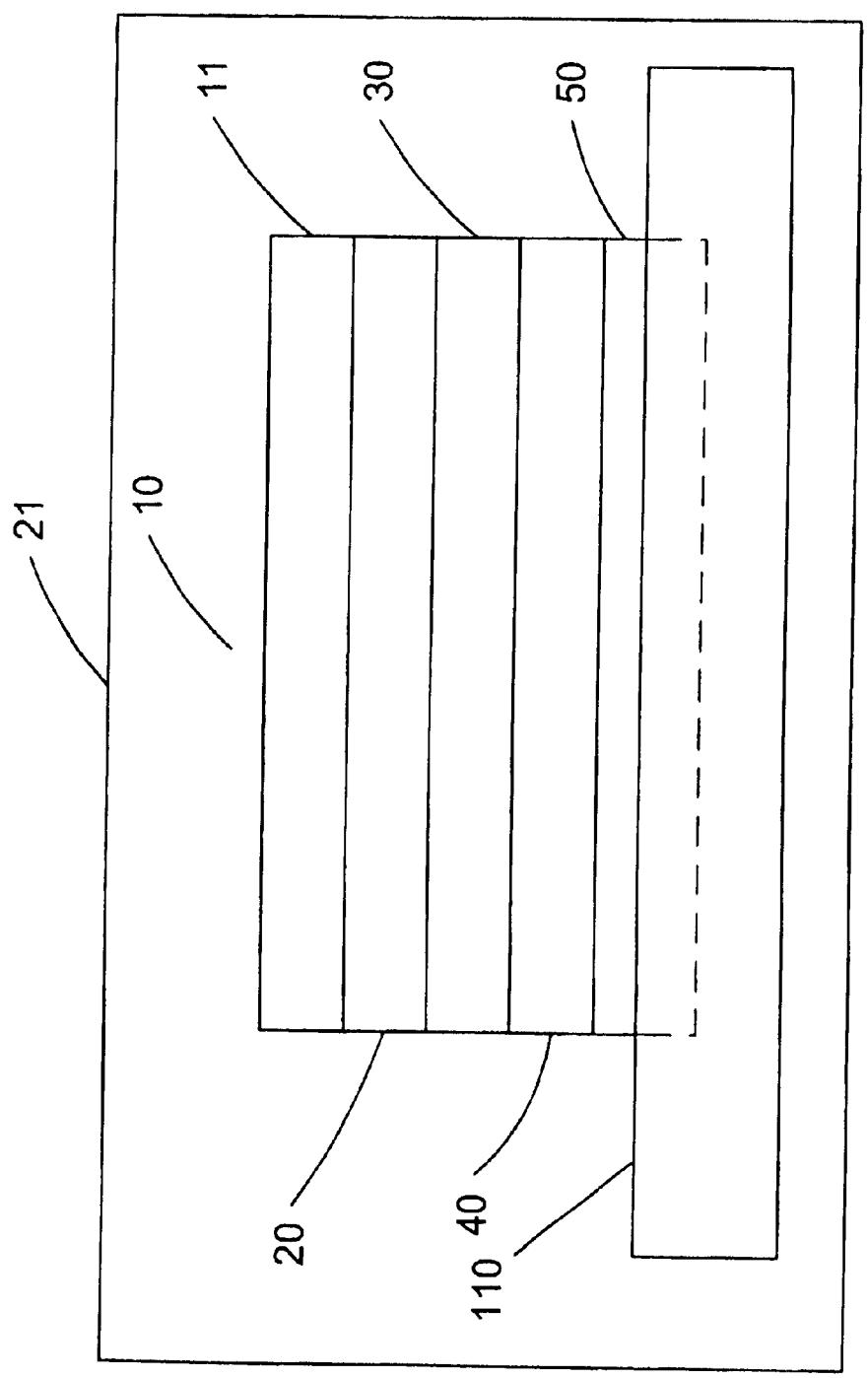
FIG. 2 is a non-exploded sectional view of the scaffold depicted in FIG. 1.
Figure 3:
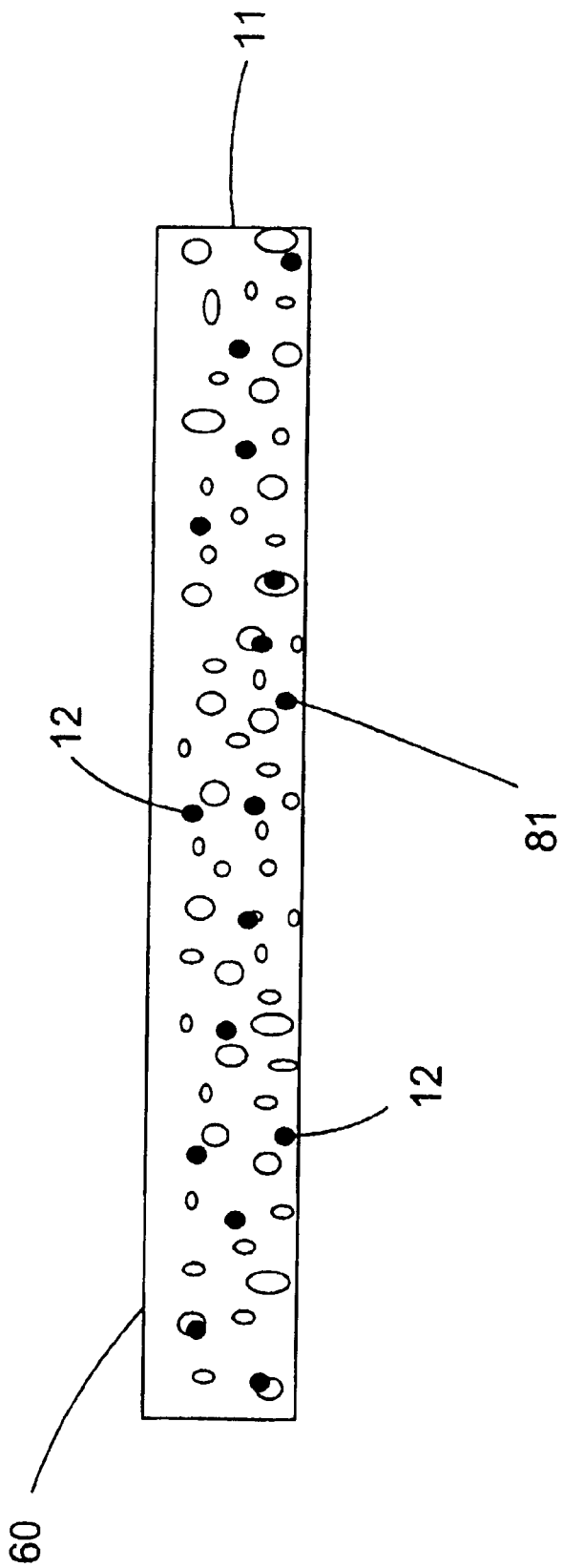
FIG. 3 is a schematic representation of one preferred base layer of the scaffold of FIG. 1.
Figure 4:
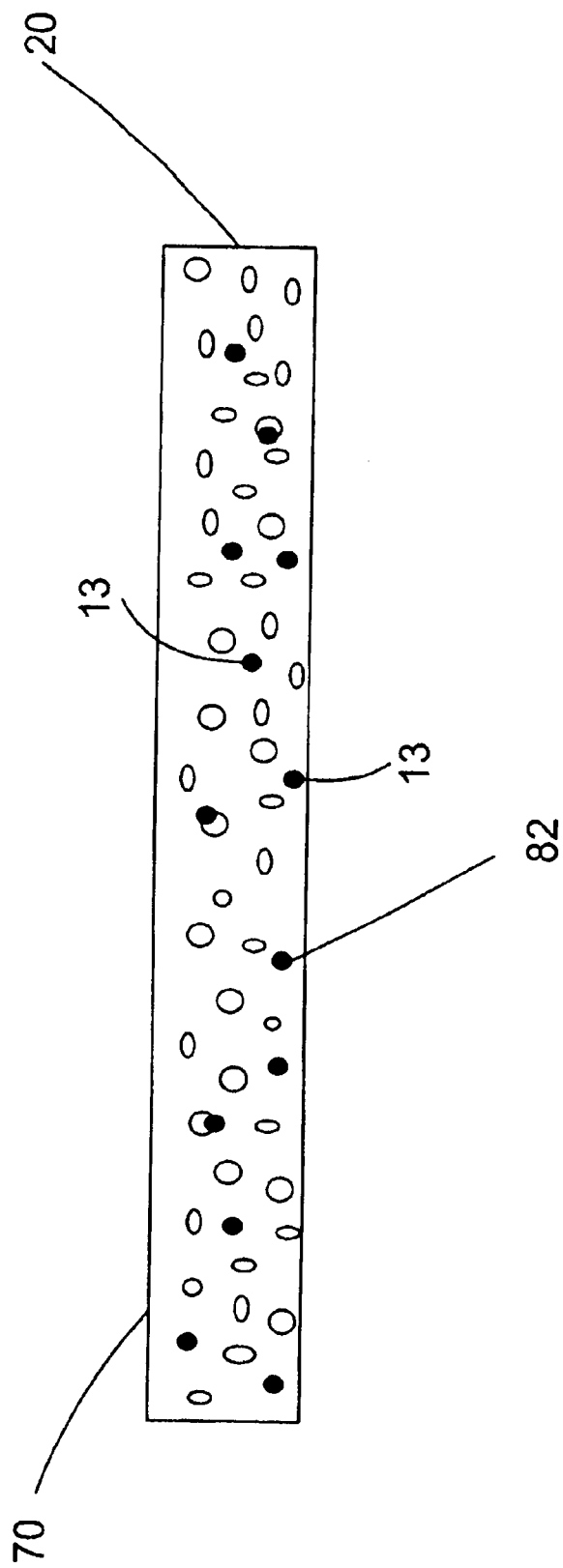
FIG. 4 is a schematic representation of one preferred second layer of the scaffold of FIG. 1.
Figure 5:
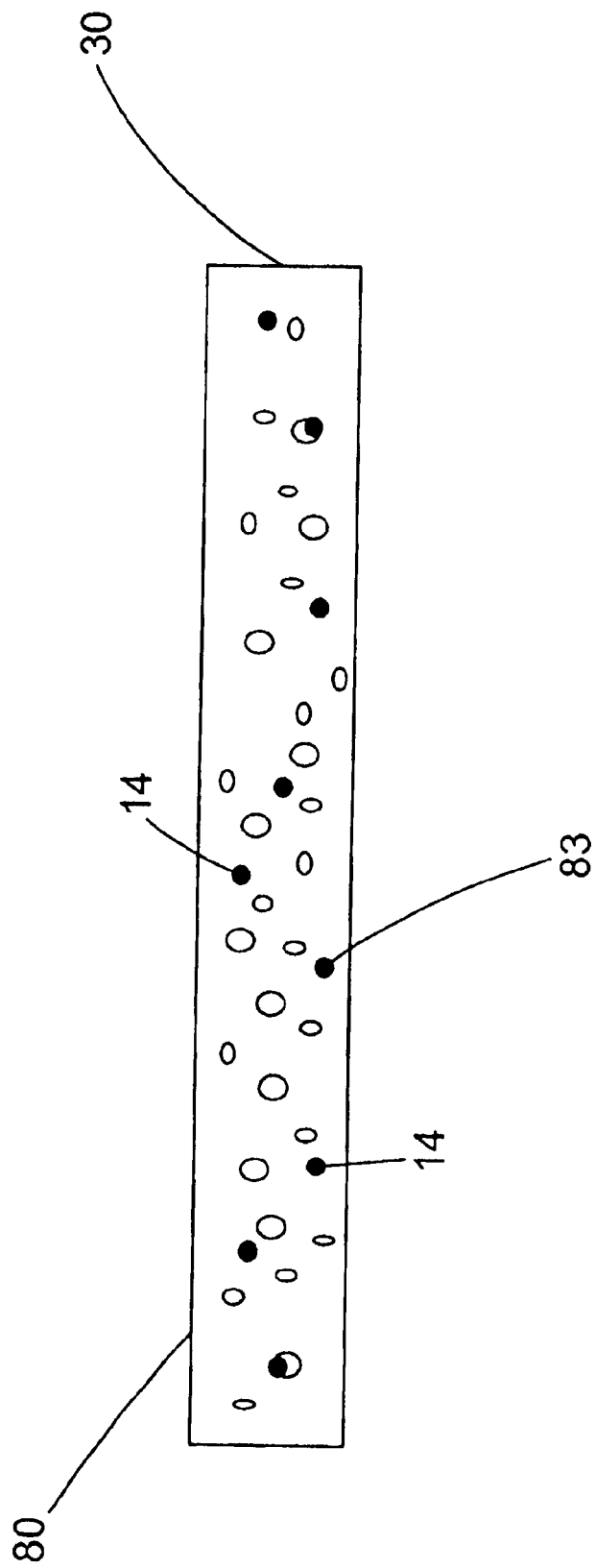
FIG. 5 is a schematic representation of one preferred third layer of the scaffold of FIG. 1.
Figure 6:
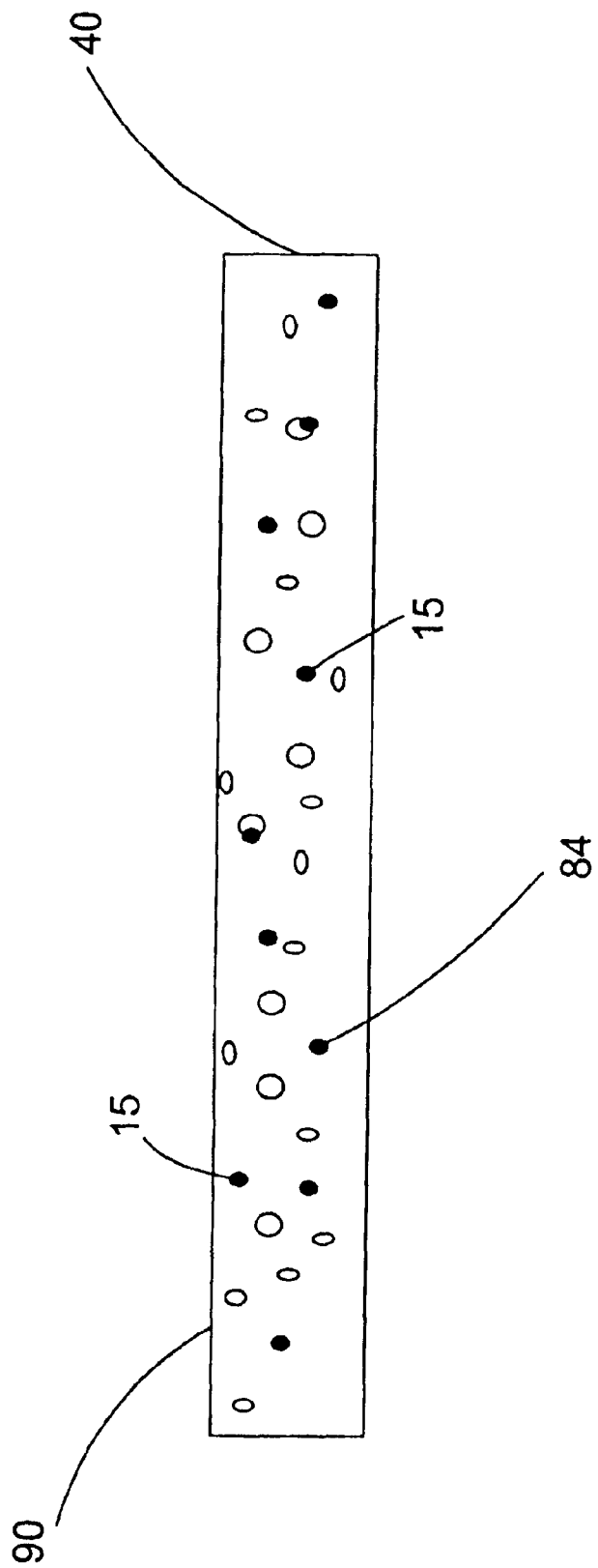
FIG. 6 is a schematic representation of one preferred fourth layer of the scaffold of FIG. 1.
Figure 7:
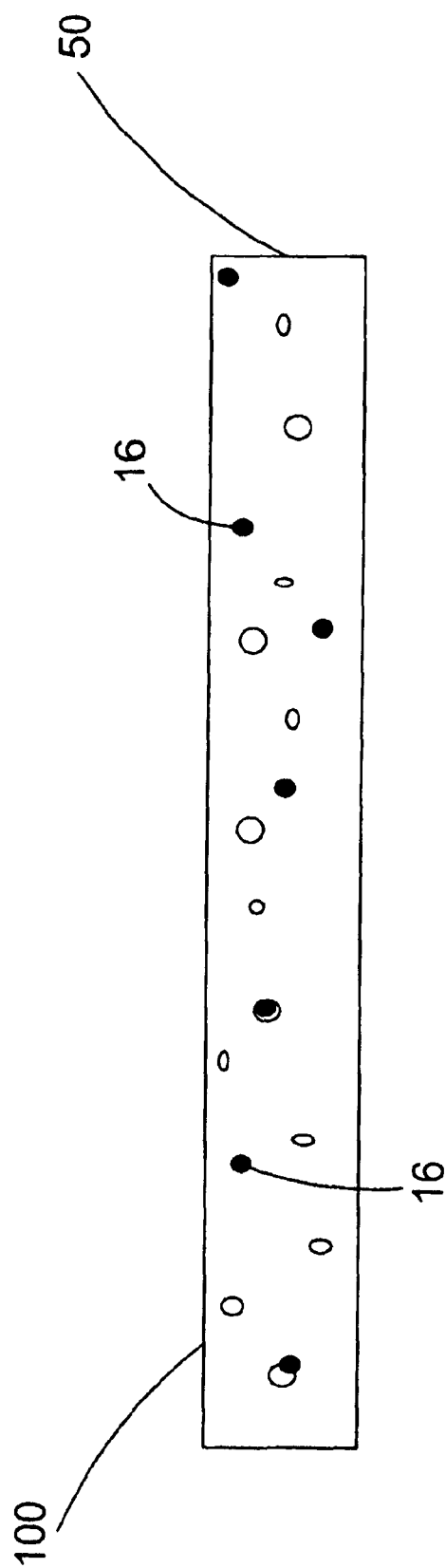
FIG. 7 is a schematic representation of one preferred fifth layer of the scaffold of FIG. 1.

FIG. 2 is an unexploded view of the scaffold 10, illustrating how layers 11, 20, 30, 40, and 50 are contiguous with each other. Referring to FIG. 2, the scaffold 10 is preferably an integral structure sealed together forming one continuous body.

In the embodiment depicted in FIG. 1, surfaces 60, 70, 80, 90 and 100 of layers 11, 20, 30, 40, and 50, respectively, are preferably coated with a biological sealant, such as fibrin, forming a composite osteochondral graft. One may use other biological sealants known to the art. Reference may be had, e.g., to U.S. Pat. Nos. 6,045,570, 5,736,132, 5,549,904, 5,702,715, 6,022,361, and the like. The entire disclosure of each of these United States patents is hereby incorporated by reference into this specification.

In another preferred embodiment, the sealants are applied after the application of mechanical stimulation and magnetic fields and also after a significant amount of cell growth and differentiation has been noticed within each layer. This is to ensure that each individual layer has developed independently and distinctively from the other. The sealant may then be applied, and the layers sealed together to form the three-dimensional construct of the organ.

In one embodiment, the layers 11, 20, 30, 40, and 50 are preferably made of natural marine coral or a coralline hydroxyapatite ceramic (HA). It is believed that a hydrothermal chemical exchange converts the original calcium carbonate exoskeleton of coral into a completely inorganic replica of hydroxyapatite. The three-dimensional macroporous structure formed mimics natural cancellous bone and facilitates tissue and vascular invasion into the pore areas after implantation of the coral. Experimental and clinical data show excellent vascular invasion, biocompatibility, and osteoconductivity of the coral when used as a bone graft substitute. Other materials that may be used for the scaffold include but are not limited to aluminum oxide and phosphate-based ceramics.

In one embodiment, coralline hydroxyapatite ceramic material is used. This material is well known to those skilled in the art. Reference may be had, e.g., to U.S. Pat. Nos. 6,063,117, 6,049,026, 5,024,084, 6,190,412, 6,139,574, 6,176,874, 6,065,476, and the like. The entire disclosure of each of these United States patents is hereby incorporated by reference into this specification.

In one embodiment, and referring again to FIG. 1, the scaffold 10 and its layers 11, 20, 30, 40, and 50 are coated with extracellular matrix proteins in the form of fibronectin, collagen and laminin to ensure binding of cell to the scaffold structure. Intracellular effects of the extracellular proteins are elicited via the binding of the downstream cell surface receptors through. The actions of integrin receptors for extracellular matrix and receptors for growth factors are synergistic in regulating gene transcription, cellular differentiation and function. In vitro studies show that autocrine bone morphogenetic protein production as well as intergrin-mediated cell-collagen interactions are synergistic, and are both required for osteoblast differentiation (Journal of Bone and Mineral Research 17(1): 110–110 Jan. 2002) and regulating function (American Society of Bone and Mineral Research 1999, Vol 14, Iss 7 pp 1075–1053). The data suggest that a signal(s) from collagen integrin receptors regulates the response to bone morphogenetic proteins downstream of bone morphogenetic protein receptor-IB and upstream of early markers of osteoblast differentiation. In addition, the use of a bone morphogenetic protein-2 retroviral expression vector in a multipotential mesenchymal cell line is highly effective at inducing a chondrocyte phenotype in vitro, whereby the phenotype was only seen in cells known to have efficient transfection of the gene. These findings provide a framework for the optimization of chondrogenesis in culture using mesenchymal stem cells and retroviral gene transfer.

The significance of the interaction of integrins with extracellular matrix proteins, growth factors and their receptors in cellular processes is well known to those skilled in the art. Reference may be had, e.g., to U.S. Pat. Nos. 6,300,080, 6,177,542, 5,981,478, 5,912,234, 5,599,676, 5,536,814, and the like. The entire disclosure of each of these United States patents is hereby incorporated by reference into this specification.

In another embodiment, and referring to FIGS. 3 through 7, the scaffold layers 60, 70, 80, 90, and 100 are preferably sealed with tissue sealants, which can be of any biocompatible material including but not limited to fibrin sealants, collagen and thrombin, cyanoacrylates, polyethylene glycol polymers, and cross-linked albumin. These and other tissue sealants are well known to those skilled in the art and are described, e.g., in U.S. Pat. Nos. 6,200,587, 6,117,425, 6,063,297, 5,788,622, 5,585,007, 6,197,625, 6,162,241, 6,054,122, and the like. The entire disclosure of each of these United States patents is hereby incorporated by reference into this specification.

In one embodiment, depicted in FIG. 1 et seq., the scaffold 10 is substantially the same size of the structure/organ it is meant to replace.

In one embodiment, and referring to FIG. 2, the scaffold 10 is seeded with progenitor cells, embryonic mesoderm-derived mesenchymal cells or bone marrow stromal cells (not shown in FIG. 2, but see FIGS. 3 through 7) for bone relating to the organ it is meant to replace. Different cells 12, 13, 14, 15, and 16 (see FIGS. 3 through 7) are utilized in layers 11, 20, 30, 40, and 50, respectively. In general, each of such different layers 11, 20, 30, 40, and 50 will contain cells of a different type than in any other of such layers. Each cell type in each layer may also be genetically engineered to express or overexpress different genes and their protein products, for example the growth factors of the TGF□ superfamily. Thus, e.g., according to U.S. Pat. No. 6,077,987, for repair of bone, a gene (or genes) encoding bone morphogenic protein is transfected into periosteal cells. The transfected periosteal cells then express the bone morphogenic protein in culture and promote bone repair as a function of the expressed bone morphogenic protein. Cells can be transfected using any appropriate means, including viral vectors, chemical transfectants, or physico-mechanical methods such as electroporation and direct diffusion of DNA. Genes can encode any useful protein, for example, a specific growth factor, morphogenesis factor, a structural protein, or a cytokine which enhances the temporal sequence of wound repair, alters the rate of proliferation, increases the metabolic synthesis of extracellular matrix proteins, or directs phenotypic expression in endogenous cell populations. Representative genes encoding proteins include bone growth factor genes, cartilage growth factor genes, nerve growth factor genes, and general growth factors important in wound healing, such as platelet-derived growth factor (PDGF), vascular endothelial growth factor (VEGF), insulin-like growth factor (IGF-1), epidermal growth factor (EGF), basic fibroblast growth factor (FGF), endothelial derived growth supplement. These and other methods of genetic engineering are well known to those skilled in the art and are described, e.g., in U.S. Pat. Nos. 5,763,416, 5,942, 496, 5,962,427, 156,304, 6,315,992 and the like. The entire disclosure of each of these United States patent is hereby incorporated by reference into this specification.

Means for seeding cells in layers of coralline hydroxyapatite ceramic and other materials are well known. Reference may be had, e.g., to U.S. Pat. Nos. 6,306,169, 6,277, 151, 6,1563,292, 6,143,293, 6,132,463, 5,902,741, and the like. The entire disclosure of each of these United States patents is hereby incorporated by reference into this specification.

In the case of bone, these seeded cells will be of chondrocytic and/or osteoblastic lineage. Seeding in a three-dimensional scaffold requires high yield to maximize cell utilization, and high kinetic rate to minimize the time in suspension for the anchorage-dependent and shear-sensitive cells and high spatially uniform distribution of attached cells for rapid and uniform tissue growth.

In another embodiment, drugs and substances that initiate, enhance and maintain cell proliferation and survival are preferably incorporated within the layers 11 and/or 20 and/or 30 and/or 40 and/or 50. By way of illustration, suitable drugs include growth factors (such as insulin-like growth factors [IGF I and IGF II]), transforming growth factors beta superfamily (TGF-β), fibroblast growth factors (FGF), platelet derived growth factors, and other growth factors, such as epidermal growth factors and vascular endothelial growth factors. These and other growth factors are well known to those skilled in the art and are described, e.g., in U.S. Pat. No. 5,455,041, the entire disclosure of which is hereby incorporated by reference into this specification. As is disclosed in this patent, periodontal therapies are directed at arresting the progression of the pathological alterations due to periodontal disease, as well as promoting the repair or regeneration of the periodontal wounds. Such therapies include wound and bone regeneration using purified growth factors, using growth factors in combination with dexamethasone to enhance the mitogenic effect of the growth factor, and using root surface demineralization. For an excellent review see Lowenguth and Blieden, 1993, Periodontology 2000, 1:54–68); and the use of periodontal barriers such as membranes (Magnuson et al., U.S. Pat. No. 4,961,707), microparticles (Jernberg, U.S. Pat. Nos. 5,059, 123 and 5,197,882), biodegradable polymers (Dunn et al., U.S. Pat. No. 5,077,049) and biocompatible porous material comprising expanded polytetrafluoroethylene (Scantlebury et al., U.S. Pat. No. 5,093,179). The entire disclosure of each of these United States patents is hereby incorporated by reference into this specification.

Growth factors, particularly platelet-derived growth factors (PDGF) and insulin-like growth factor (IGF-1) are known to stimulate mitogenic, chemotactic and proliferative (differentiation) cellular responses.

Insulin like growth factors aid in the synthesis of more osteobalsts, modulating their behavior during remodeling, promoting synthesis of bone matrix, and up regulating Type I collagen (necessary for cartilage and bone formation). Transforming growth factors-beta superfamily affect cell growth and proliferation by controlling apoptosis (cell death), differentiation, and induction of new gene expression. Fibroblast growth factors are synthesized by osteoblasts, can be released during bone resorption, and have been known to stimulate bone resorption. Platelet derived growth factor has the ability to act in a paracrine or autocrine manner and promote proliferation and collagen synthesis. Cytokines, another group of growth factors, include interleukin-1 (IL-1), prostaglandins and leukotrienes and stimulate both the humoral and cellular immune responses.

In one embodiment, and referring again to FIG. 1, in order to initiate chondrogenesis and osteogenesis, cartilage-derived morphogenetic proteins (cDMPs) and bone morphogenetic proteins (BMP) are added to the scaffold and, in particular, layers 11 and/or 20 and/or 30 and/or 40 and/or 50. This aids in chemotaxis, mitosis and differentiation of the cells.

Morphogenetic proteins are well known to those skilled in the art and are described, e.g., in U.S. Pat. Nos. 6,315,992, 6,302,913, 6,280,474, 6,261,586, 6,258,778, 6,228,117, and the like. The entire disclosure of each of these United States patents is hereby incorporated by reference into this specification.

In another embodiment, means for ensuring localization of growth factors is included within the scaffold 10 and, in particular, within the layers 11 and/or 20 and/or 30 and/or 40 and/or 50. In one embodiment, these means include tethered growth factor effector molecules. Reference may be had to U.S. Pat. No. 6,045,818, the entire disclosure of which is hereby incorporated by reference into this specification. This patent discloses and claims compositions with tethered growth effector molecules, and methods of using these compositions for growing cells and tissues. As is disclosed in this patent growth effector molecules, including growth factors and extracellular matrix molecules, are flexibly tethered to a solid substrate. The compositions can be used either in vitro or in vivo to grow cells and tissues. By tethering the growth factors, they will not diffuse away from the desired location. By making the attachment flexible, the growth effector molecules can more naturally bind to cell surface receptors. A significant feature of these compositions and methods is that they enhance the biological response to the growth factors. The method of this patent provides other advantages over the traditional methods, in which growth factors are delivered in soluble form: (1) the growth factor is localized to a desired target cell population; and (2) significantly less growth factor is needed to exert a biologic response.

In one embodiment, and referring to FIG. 2, the scaffold 20 will be disposed within in a bioreactor 21. The bioreactor 21 provides an in-vitro environment that embodies chemical and mechanical signals that regulate tissue development and maintenance in vivo. The bioreactor culture vessels may include but are not limited to spinner flasks, rotating vessels, a perfused chamber, or a perfused column. The bioreactor will have the ability to apply a variety of (mechanical) signals to the cells.

Bioreactors, especially bioreactors used for tissue regeneration processes, are well known. Reference may be had, e.g., to U.S. Pat. Nos. 6,306,169, 6,197,575, 6,080,581, 5,677,355, 5,433,909, 5,898,040, and the like. The entire disclosure of each of these United States patents is hereby incorporated by reference into this specification.

As is known to those skilled in the art, bioreactors help in establishing spatially uniform cell distribution on three-dimensional scaffolds, maintain desired concentrations of gases and nutrients in the culture medium, provide sufficient mass transfer to growing tissues, and expose developing tissues to physical stimuli.

One may use any of the culturing systems known to those skilled in the art for cell seeding and/or bioreactor cultivation methods.

Cell seeding culturing systems include, e.g., monolayer culture systems, three-dimensional culture systems utilized with synthetic scaffolds, three-dimensional culture systems used with biological scaffolds, and the like. Reference may be had, e.g., to U.S. Pat. Nos. 6,277,151, 6,197,575, 6,139,578, 6,132,463, 5,902,741, 5,629,186, and the like. The entire disclosure of each of these United States patents is hereby incorporated by reference into this specification.

Various bioreactor cultivation methods may be used in connection with culturing systems. Thus, e.g., one may utilize bioreactors with slow turning lateral vessels, with high aspect ratio vessels, with rotating wall perfused vessels, with perfused columns, with perfused chambers, and the like. These and other bioreactor cultivation methods are well known. Reference may be had, e.g., to U.S. Pat. Nos. 5,981,211, 5,888,815, 5,064,764, 5,015,585, 4,743,189, 4,861,661, and the like. The entire disclosure of each of these United States patents is hereby incorporated by reference into this specification.

In another embodiment, the cell culture bioreactor may also have the capability to mechanically stimulate cells. Devices for mechanically stimulating cells are well known and are described, e.g., in U.S. Pat. No. 4,851,354. This patent discloses an apparatus useful for studying cells in culture under conditions, which reproduce their natural, in vivo mechanical environment. Use of the apparatus of this patent enables one to study the changes in the biochemistry and physiology of cultured cells under conditions of mechanical strain as compared to cells grown conventionally under quiescent conditions.

As is indicated in U.S. Pat. No. 4,851,354, the mechanical stimulation of cells is believed to influence the biochemistry and physiology of cells, in particular, enhanced production and, therefore, improved harvesting efficiency of biochemical products from these cells. Various systems have been proposed previously for growing cells in culture. One typical prior art system (Leung, D., et al, Science 191:475–477, 1976), attempts to uniaxially elongate smooth muscle cells in culture. In another typical prior art system (Davies, P. et al, J. Clin. Invest. 73:1121–1129, 1984), cells in culture are subjected to a uniform shear strain, constant in magnitude and direction.

The system of U.S. Pat. No. 4,851,354 comprises an airtight well having an optically transparent compliant base of a biologically compatible material on which cells may be grown and an optically transparent, removable cap, and an aported, airtight reservoir coupled with said well beneath said compliant base, which reservoir has an optically transparent base and which reservoir can be filled with pressurizing medium to create cyclic variations in hydrostatic pressure beneath said compliant base, causing said compliant base to deform and thereby exert a substantially uniform biaxial strain on the cells attached thereto. The entire disclosure of this United States patent is hereby incorporated by reference into this specification.

By way of further illustration, other means for mechanically stimulating cells are described in U.S. Pat. No. 6,306,169 (compressive strain applied to chondrocytes seated in agarose gel), U.S. Pat. Nos. 6,117,674, 5,858,783 (stretching of embryonic avian muscle cells), U.S. Pat. Nos. 5,846,807, 5,496,722, 5,264,906, and the like. The entire disclosure of each of these United States patents is hereby incorporated by reference into this specification.

Figure 8:
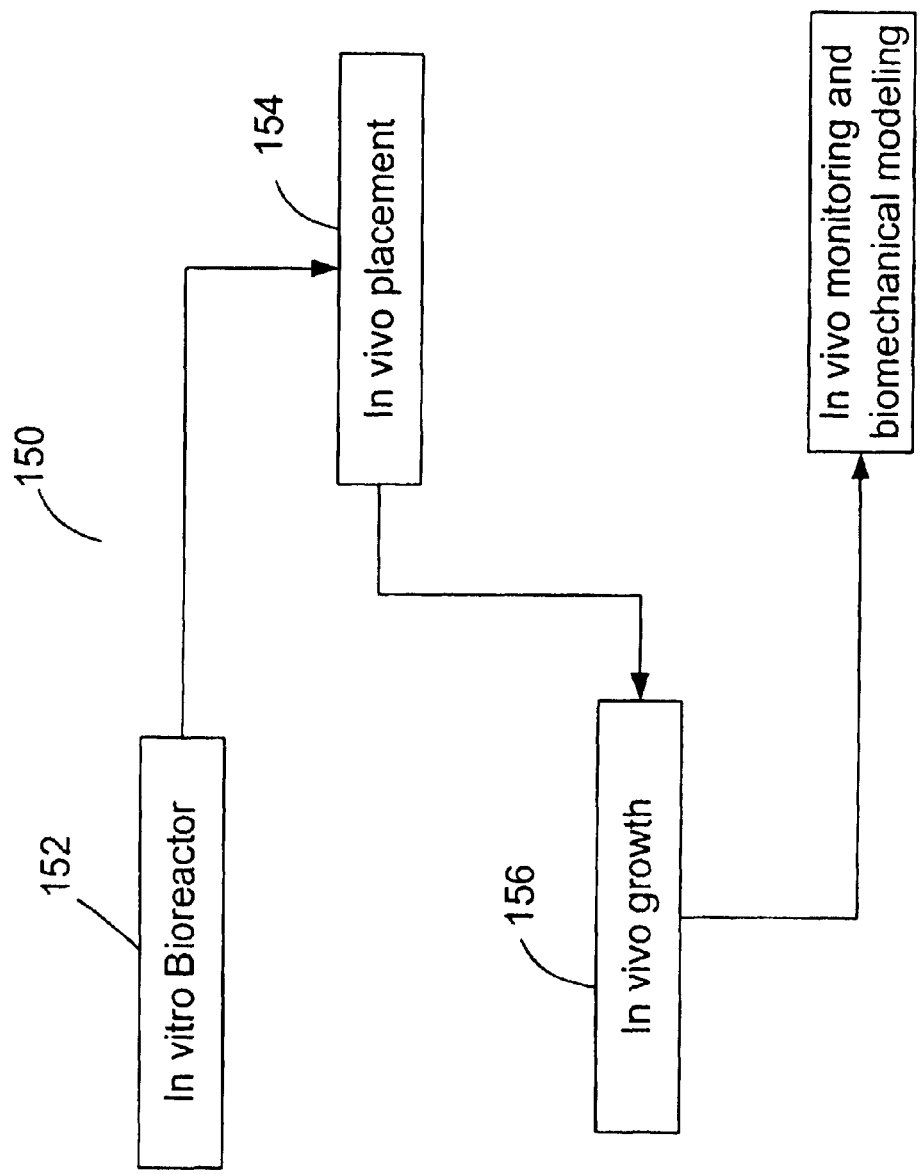
FIG. 8 is a flow diagram of steps involved from growth of an artificial organ to its placement and functionality in a living body.
Figure 9:
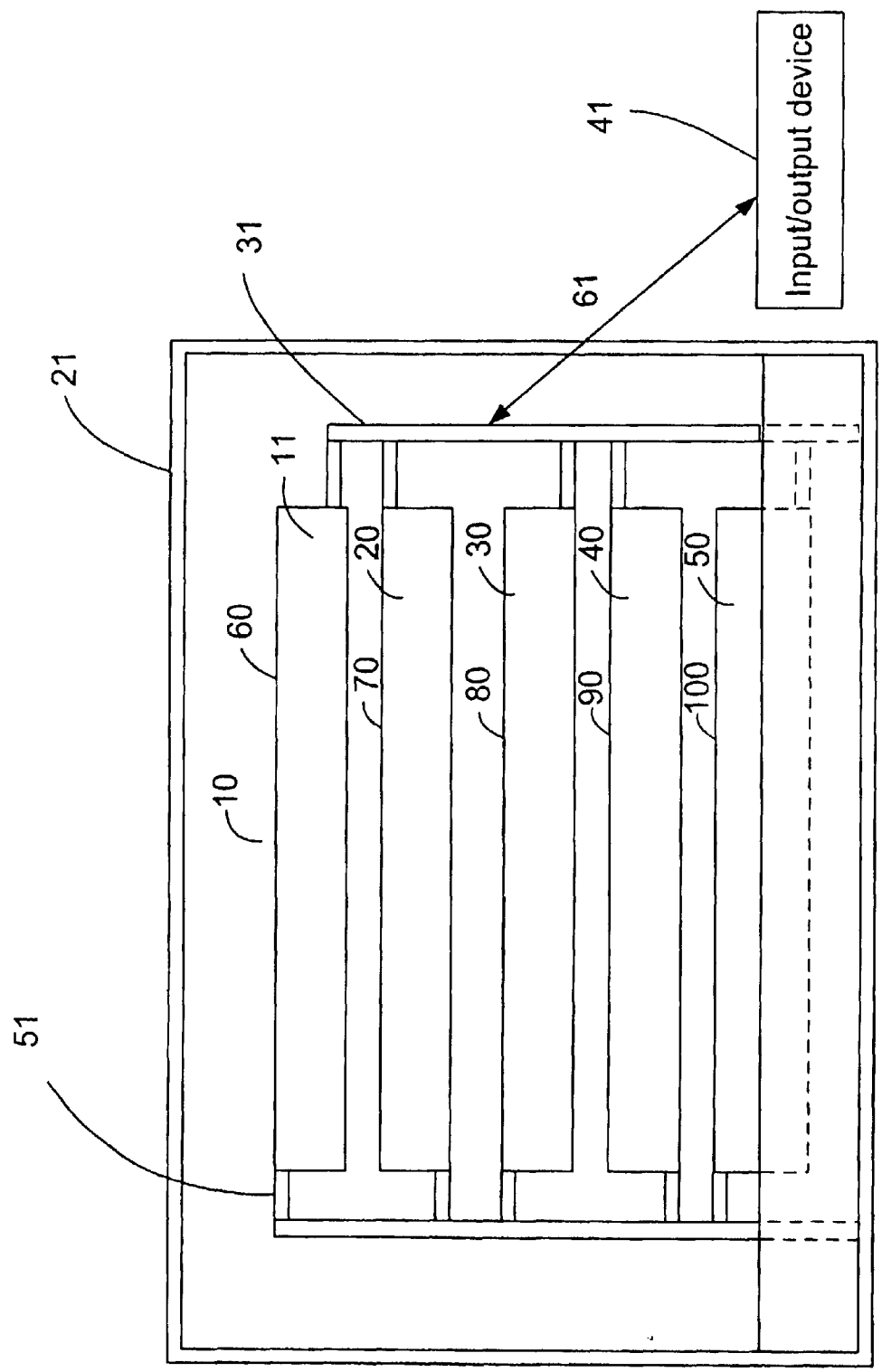
FIG. 9 is a diagram of a mechanical stimulus transducer for a bioreactor system.

As is illustrated in FIG. 8, and in one preferred process 150 of the invention, the layers 60 are stimulated in a bioreactor in step 152 and, thereafter, in step 154 surgically placed within a living organism. In step 156, the layers so disposed within such organism adapt to the environment they have been placed within and grow in vivo. In step 158, such in vivo growth is monitored.

Figure 10:
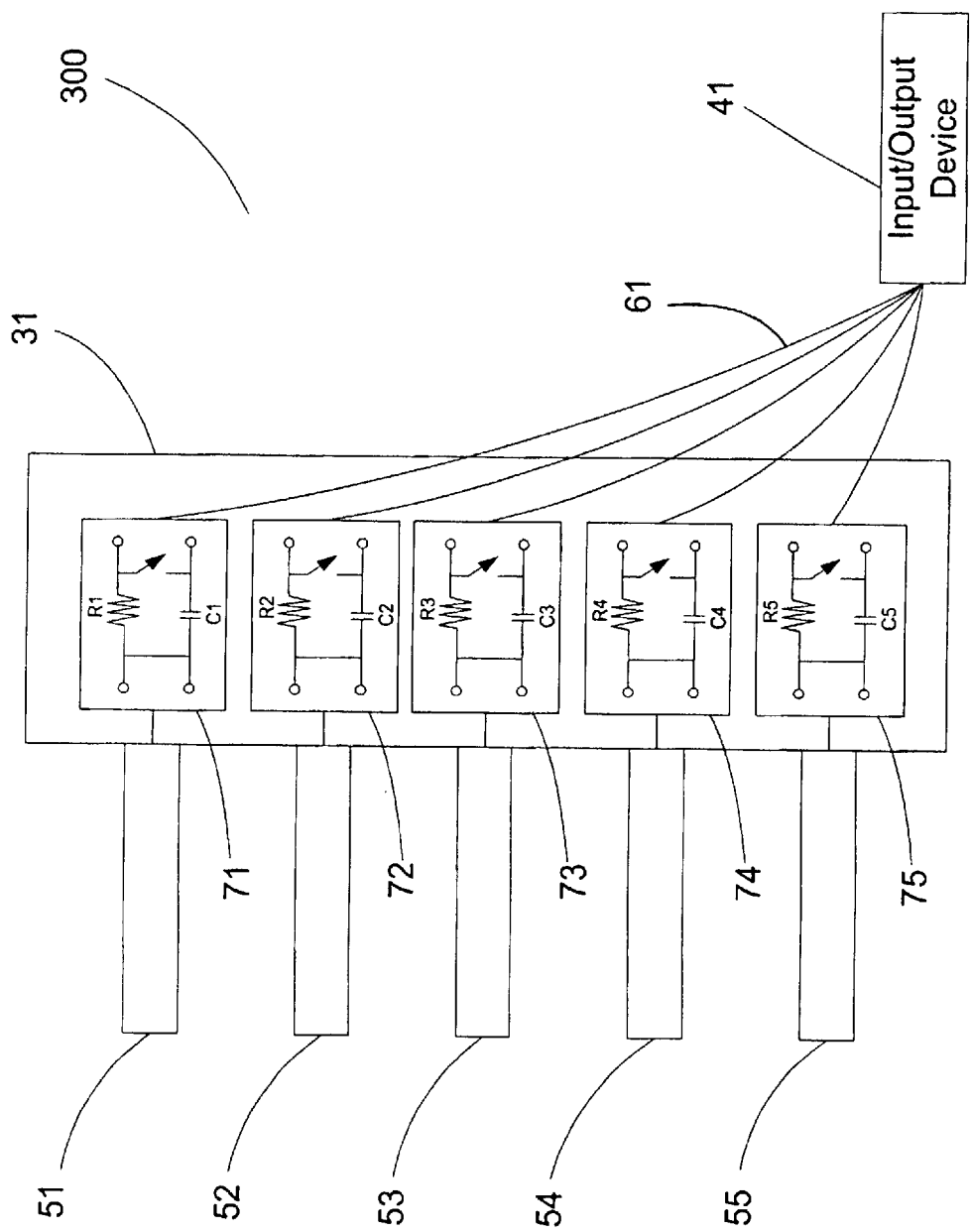
FIG. 10 is an exploded view of one preferred embodiment of the input/output device.

The stretching and contracting at specified frequencies is preferably provided by a mechanical stimulus transducer 31, one embodiment of which is illustrated in FIG. 10. It is known that the mechanical stretching of cell cultures can lead to changes in osteoblast or chondrocyte proliferation or differentiation. For example an article appearing in the Journal of Orthopedic Research (2001 March; 19(2):286–93) discloses that cell alignment is induced by cyclic changes in cell length. This article also discloses that many types of cells, when grown on the surface of a cyclically stretched substrate, align away from the stretch direction. Although cell alignment has been described as an avoidance response to stretch, the specific deformation signal that causes a cell population to become aligned has not been identified. Planar surface deformation is characterized by three strains: two normal strains describe the length changes of two initially perpendicular lines and one shear strain describes the change in the angle between the two lines.

In one embodiment, stimulator assembly 300 (see FIG. 10) is attached to an input/output device 41 that has the ability to control the mechanical stimulus being imposed on the cells in the scaffold.

In the embodiment depicted in FIG. 10, a series of resonant circuits 71, 72, 73, 74, and 75 are individually controlled via input/output device 41 and leads 61 to selectively provide mechanical energy to clamps 51, 52, 53, 54, and 55 and to cause them to provide energy to layers 50, 60, 70, 80, 90, and 100 in a specified manner or manners.

In another embodiment, a method is provided whereby the proliferation and differentiation of the different cell layers is controlled via mechanical perturbations. In this embodiment, cell growth and differentiation are not only being regulated using genetic engineering but also mechanically.

In one embodiment, one may use the mechanical stimulator described in an article by Michael J. Yost et al. ("Design and construction of a uniaxial cell stretcher," Am. J. Physiol. Heart Circ. Physiol, 279: H3124–3130, 2000). In this article, the authors describe an in vitro mechanical cell stimulator used for the study of the effect of mechanical stimulation on anchorage-dependent cells. A new mechanical cell stimulator was developed which used stepper motor technology and computer control to achieve a high degree of accuracy and repeatability. This device also used high-performance plastic components that had been shown to be non-cytotoxic, dimensionally stable, and resistant to chemical degradation from common culture laboratory chemicals. These studies yielded a new and improved mechanical cell stimulator and demonstrated that mechanical stimulation has an effect on the expression of beta(1)-integrin.

In another embodiment, the cell culture bioreactor also preferably comprises means for electromagnetically stimulating the cells with the presence of an electromagnetic field. Experimental research shows that bone cell proliferation can be induced by pulsed electromagnetic fields (PEMF), as is the stimulation of matrix formation and calcification (Biochemical and Biophysical Research Communications 250, 458–461 1998).

PEMFs can be generated by means of a Helmholz coil pair and waveform generator, such as that sold by Electro-Biology Inc. of Parsippany, N.J. This waveform generator utilizes a saw tooth waveform consisting of 4.5 millisecond bursts of pulses, repeating at 15 hertz with a peak magnetic field of 18 gauss during each 225-microsecond pulse. Furthermore, in vivo studies show that continuous exposure for 6 hours per day for 30 days to PEMF stimulates cell proliferation and bone repair (Bioelectromagnetics 20: 177–182 1999).

Devices for electromagnetcally stimulating cells are well known and are described, e.g., in U.S. Pat. No. 6,190,893. This patent discloses compositions, methods and systems provided for the stimulation of biological activities within bone marrow stromal cells by applying electromagnetic stimulation to an electroactive material, wherein the electromagnetic stimulation is coupled to the electromagnetic material. In general the invention of this patent involves attaching or associating the desired bone marrow stromal cells to or with a surface comprising an electroactive material, and thereafter applying electromagnetic radiation directly to the desired area. In the stimulation of biological activities within bone marrow stromal cells, results from inducing one or more activities include, but not limited to, gene expression, cell growth, cell differentiation, signal transduction, membrane permeability, cell division and cell signaling. In another preferred embodiments, the invention stimulates bone cell regeneration. In exemplary embodiments of the invention, the electroactive materials used are either two-dimensional substrates (such as thin films having at least one surface of an electroactive material) or three-dimensional substrates comprising a matrix having at least one surface of an electroactive material. The entire disclosure of this U.S. Pat. No. 6,190,893) is hereby incorporated by reference into this specification.

The term electromagnetic stimulation, as used in this patent application, refers to stimulation by any form of electromagnetic energy including, but not limited to, stimulation by electromagnetic radiation or pulsed electromagnetic field (PEMF).

In one embodiment, the electroactive material to be used is a material that contains pockets of electron density. This material may be conducting, non-conducting, semiconducting, or piezoelectric, to name a few. For the purposes of the present invention, preferred electroactive materials include electroactive polymers. These electroactive polymers are characterized in that they contain at least a pocket of electron density and are capable of undergoing a phase transition upon subjecting the polymer to an electromagnetic field stimulus.

Figure 11:
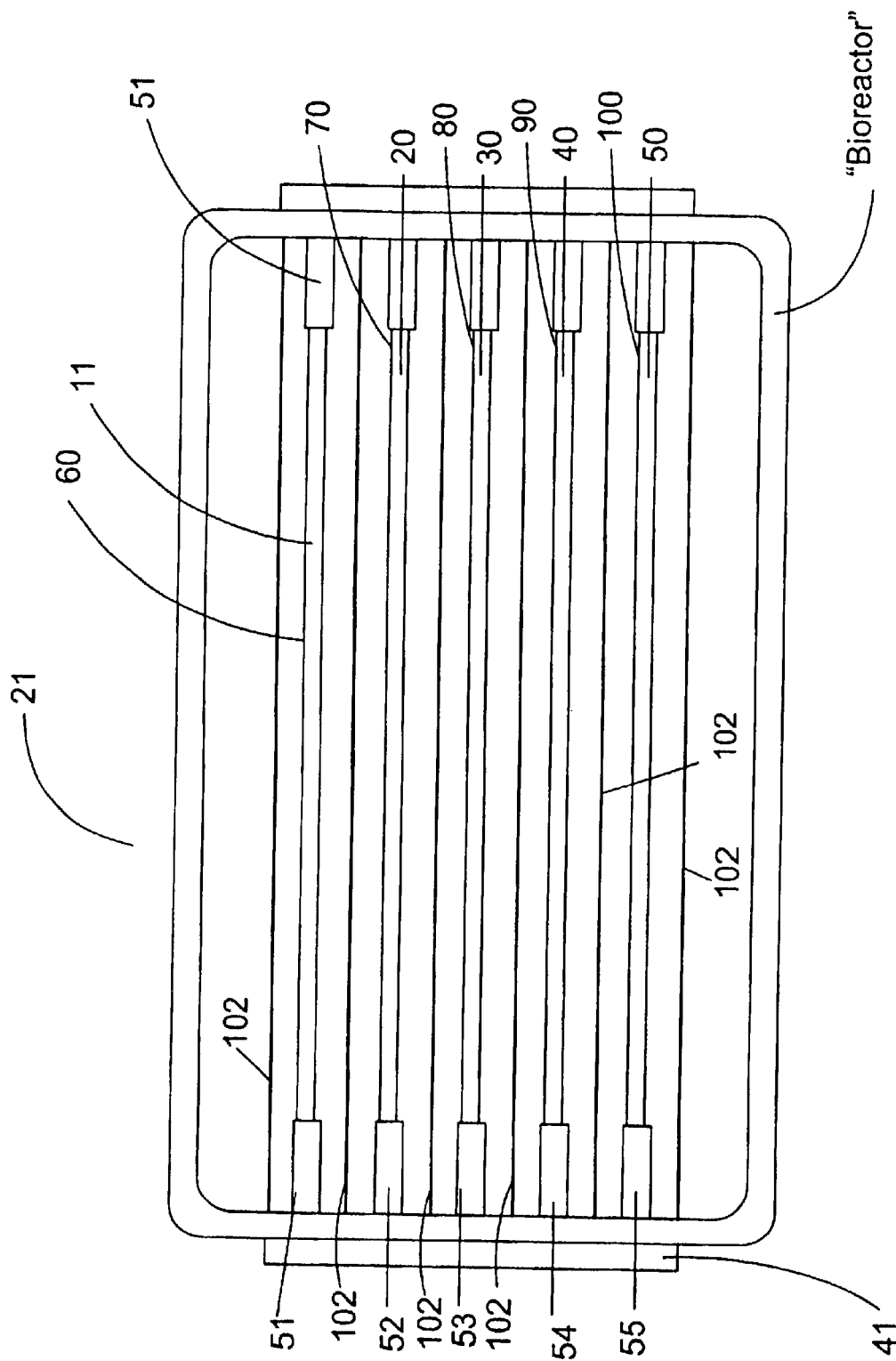
FIG. 11 is a schematic of one preferred embodiment of a system enclosed in a bioreactor.

FIG. 11 is a side view of one preferred bioreactor 21 which, in the embodiment depicted, is used to deliver mechanical stimulation to each of the layers 60, 70, 80, 90, and 100. In the embodiment depicted, these layers are not contiguous with each other during the time the mechanical stimulation is being applied; this non-contiguity is insured by the use of division panels 102. These division panels are biocompatible panels that prevent or minimize the transmission of mechanical energy from one layer to another. As will be apparent, once the mechanical stimulations of the various layers have ceased, the division panels are removed so that the layers are once again contiguous with each other.

Referring again to FIG. 11, and in the preferred embodiment depicted therein, clamps 51, 52, 53, 54, and 55 are used to hold the layers of biocompatible material in place while they are being mechanically stimulated.

Figure 12:
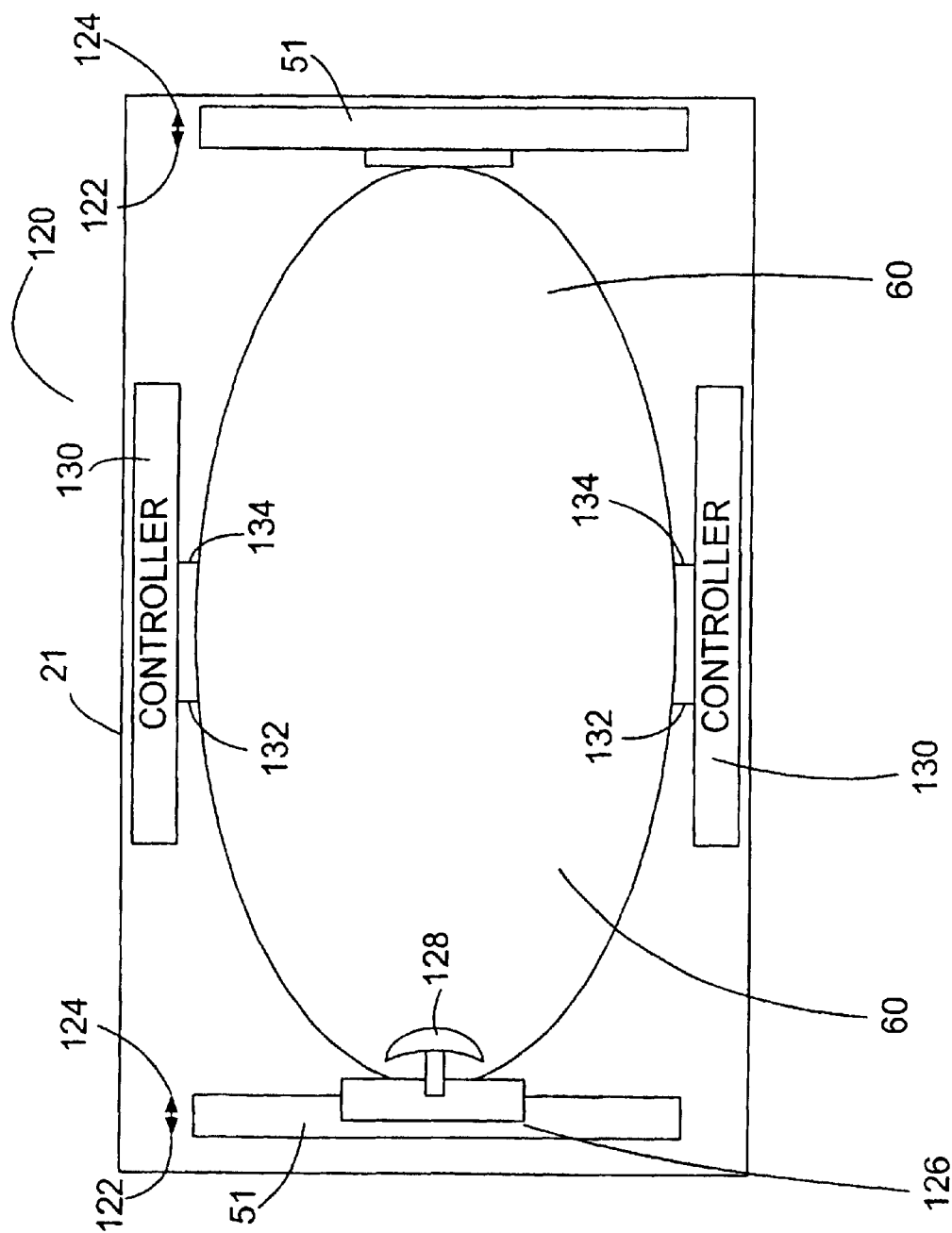
FIG. 12 is a an overhead view of one of the preferred layer of the system of FIG. 11.

FIG. 12 is a top view of a portion of a assembly 120 for mechanically stimulating layer 60. In this assembly 120, clamps 51 are moved in the direction of arrows 122 and 124. Attached to at lest one of the clamps 51 is a plunger assembly 126 that is comprised of plunger 128. As the clamp 51 moves, the plunger 128 also moves in and out of the layer 60, facilitating its mixing.

Referring again to FIG. 12, and in the preferred embodiment depicted therein, controller 130 provides electromagnetic stimulation to layer 60 via leads 132 and 134. This stimulation may be continuous and/or intermittent, and it may vary in type, intensity, and duration.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

We claim:

1. A cell-scaffold composition comprised of a first layer of biocompatible material, a second layer of biocompatible material, a third layer of biocompatible material, a fourth layer of biocompatible material, and a fifth layer of biocompatible material, wherein each of said layers is coated with a biological sealant material, wherein each of said layers is comprised of different cells, and wherein said cell-scaffold composition is disposed within a bioreactor which is comprised of means are for mechanically stimulating each of the cells in each of said layers at distinct frequencies.

2. The cell-scaffold composition as recited in claim 1, wherein said first layer of biocompatible material is comprised of an extracellular matrix composition having a porosity of from about 50 to about 90 percent.

3. The cell-scaffold composition as recited in claim 2, wherein said second layer of biocompatible material is disposed above and contiguous said first layer of biocompatible material.

4. The cell-scaffold composition as recited in claim 3, wherein said second layer of biocompatible material is comprised of angiogenic cells.

5. The cell-scaffold composition as recited in claim 4, wherein said angiongenic cells are selected from the group consisting of endothelial cells, smooth muscle cells, and mixtures thereof.

6. The cell-scaffold composition as recited in claim 4, wherein said second layer of biocompatible material has a porosity of from about 10 to about 50 percent.

7. The cell-scaffold composition as recited in claim 6, wherein said third layer of biocompatible material is disposed above and is contiguous with said second layer of biocompatible material, has a porosity of from about 5 to about 10 percent, and has an average pore diameter of from about 100 to about 600 microns.

8. The cell-scaffold composition as recited in claim 1, wherein said scaffold is comprised of a material selected from the group consisting of collagen, fibril-forming collagen, interluekin 1, ascorbic acid, Matrix Gla protein, osteocalcin, and mixtures thereof.

9. The cell-scaffold composition as recited in claim 1, comprising bone cells suspended in growth factor.

10. The cell-scaffold composition as recited in claim 9, wherein said growth factor is selected from the group consisting of insulin-like growth factor, transforming growth factor-beta, bio-morphogenetic protein, fibroblast growth factor, platelet derived growth factor, vascular-endothelial growth factor, epidermal growth factor, and mixtures thereof.

11. The cell-scaffold composition as recited in claim 1, wherein said biological sealant is fibrin.

12. The cell-scaffold composition as recited in claim 1, wherein said cell-scaffold comprises a material selected from the group consisting of natural marine coral, coralline hydroxyapatite ceramic, and mixtures thereof.

13. The cell-scaffold composition as recited in claim 1, wherein said means are for stimulating each of the cells in each of said layers at distinct frequencies is a mechanical stimulus transducer assembly.

14. The cell-scaffold composition as recited in claim 13, wherein said mechanical stimulus transducer assembly is comprised of a first means for mechanically stimulating said first layer of biocompatible material at a first frequency of vibration.

15. The cell-scaffold composition as recited in claim 14, wherein said mechanical stimulus transducer assembly is comprised of a second means for mechanically stimulating said second layer of biocompatible material at a second frequency of vibration, wherein said second frequency of vibration differs from said first frequency of vibration.

16. The cell-scaffold composition as recited in claim 15, wherein said mechanical stimulus transducer assembly is comprised of a third means for mechanically stimulating said third layer of biocompatible material at a third frequency of vibration, wherein said third frequency of vibration differs from said first frequency of vibration and said second frequency of vibration.

17. The cell-scaffold composition as recited in claim 1, further comprising means for electromagnetically stimulating said cells in said first biocompatible layer, said cells in said second biocompatible layer, said cells in said third biocompatible layer, said cells in said fourth biocompatible layer, and said cells in said fifth biocompatible layer, wherein said means for electrmagnetically stimulating provides distinct electromagnetic energy to each of said first, second, third, fourth, and fifth biocompatible layers.

18. The cell-scaffold composition as recited in claim 16, further comprising means for electromagnetically stimulating said cells in said first biocompatible layer, said cells in said second biocompatible layer, said cells in said third biocompatible layer, said cells in said fourth biocompatible layer, and said cells in said fifth biocompatible layer, wherein said means for electrmagnetically stimulating provides distinct electromagnetic energy to each of said first, second, third, fourth, and fifth biocompatible layers.

19. The cell-scaffold composition as recited in claim 17, wherein said electromagnetic stimulation of said cells is supplied intermittently to said cells.

20. The cell-scaffold composition as recited in claim 17, wherein said electromagnetic stimulation of said cells is applied continuously to said cells.

* * * * *